United States Patent
Lindahl

(10) Patent No.: US 7,645,243 B2
(45) Date of Patent: Jan. 12, 2010

(54) METHOD AND DEVICE FOR MEASURING OF OEDEMA

(75) Inventor: Olof Lindahl, Umeå (SE)

(73) Assignee: Bioresonator AB, Umeå (SE)

( * ) Notice: Subject to any disclaimer, the term of this patent is extended or adjusted under 35 U.S.C. 154(b) by 49 days.

(21) Appl. No.: 11/547,852

(22) PCT Filed: Apr. 6, 2005

(86) PCT No.: PCT/SE2005/000503
§ 371 (c)(1),
(2), (4) Date: Jan. 22, 2007

(87) PCT Pub. No.: WO2005/096936
PCT Pub. Date: Oct. 20, 2005

(65) Prior Publication Data
US 2008/0051678 A1 Feb. 28, 2008

(30) Foreign Application Priority Data
Apr. 6, 2004 (SE) .................................. 0400911

(51) Int. Cl.
*A61B 5/103* (2006.01)
*A61B 5/117* (2006.01)
(52) U.S. Cl. ...................................... 600/587; 600/595
(58) Field of Classification Search ................. 600/587, 600/595
See application file for complete search history.

(56) References Cited
U.S. PATENT DOCUMENTS
5,766,137 A 6/1998 Omata
6,186,962 B1 2/2001 Lloyd et al.

FOREIGN PATENT DOCUMENTS
WO 03/096872 11/2003

OTHER PUBLICATIONS

Jalkanen et al., Prostate tissue stiffness as measured with a resonance sensor system: a study on silicone and human prostate tissue in vitro, Jun. 10, 2006, Med Bio Eng Comput, 44:593-603.*
Lindahl, et al., Impression technique for the assessment of oedema: comparison with a new tactile sensor that measures physical properties of tissue, Jan. 1995, Medical and Biological Engineering and Computing, 33, 27-32.*
International Search Report for PCT/IB2005/000503 mailed Jun. 27, 2005.

* cited by examiner

*Primary Examiner*—Max Hindenburg
*Assistant Examiner*—Emily M Lloyd
(74) *Attorney, Agent, or Firm*—Nixon & Vanderhye P.C.

(57) ABSTRACT

A method and apparatus for measurement and distinguishing between brawny and pitting oedema comprises a measurement head including a tactile sensor to measure a first characteristic of the oedema and a force decay sensor mounted adjacent the tactile sensor, to measure a second characteristic of the oedema so as to distinguish brawny oedema from pitting oedema. The tactile sensor may be a resonance oscillating sensor which may determine frequency shift, and the forced decay sensor may provide information regarding the degree of displaced fluid as a measure of pitting oedema through measurement of decay of force.

16 Claims, 1 Drawing Sheet

METHOD AND DEVICE FOR MEASURING OF OEDEMA

This application is the US national phase of international application PCT/SE2005/000503 filed 6 Apr. 2005, which designated the U.S. and claimed priority of SE 0400911-4 filed 6 Apr. 2004, the entire contents of each of which are hereby incorporated by reference.

FIELD OF THE INVENTION

The present invention concerns a method and a device for measurement and assessment of oedema, especially with regard to a combination of the two types of oedema called pitting oedema and non-pitting or brawny oedema.

BACKGROUND OF INVENTION/KNOWN TECHNOLOGY

Oedema—"swelling"—is a classic symptom of illness. The presence of oedema can be used as in indicator of various kinds of illness, such as heart and kidney disease, thrombosis, burns and lymph circulation disorder. For patients, oedema involves a number of inconveniences/problems, such as pain, change in centre of gravity leading to back problems and a general impairment to quality of life. Consequently, there is a need for measuring equipment to assess an oedema and measure how oedema is reduced by various treatments in a hospital. Oedema can generally be divided in to "pitting oedema" and "brawny oedema". Brawny oedema arises when the fluid that causes the swelling remains inside the cells and not between them, as is the case with pitting oedema. Brawny oedema can also arise when the fluid causing the swelling is located between the cells but has coagulated due to the precipitation of fibrinogen. Often, pitting oedema and brawny oedema arise simultaneously in the same patient and it is known in literature that pitting oedema often turns into brawny oedema after a time.

Problems within Known Technology

Current methods of measuring oedema are principally designed to indirectly measure the volume of an oedematous (swollen) extremity and compare it with the volume of the corresponding normal extremity (volumetry). For example, such measurements for arm oedema are taken by placing the swollen arm into a cylinder full of water and then measuring the weight of the overflowing water. The same procedure is repeated with the normal arm and the difference in weight of the overflowing water gives a measure of the size of the oedema. Understandably, this method is very imprecise and small differences in the size of an oedema cannot be measured. Neither can the distribution of different types of oedema nor their location be determined with volumetry.

In recent years there have been a number of identometers/tonometers presented in the literature. These measure the occurrence of pitting oedema locally by e.g. depressing the skin at the site of the swelling and holding a depth of depression for a certain time of measurement, e.g. 20 seconds. The force required to maintain the depth of depression is registered and will become lower during the time of measurement depending more or less on how much of the free flowing oedema fluid that is displaced in the tissue under pressure.

One example of the tonometric method is the impression method that presses a circular measuring plate (e.g. D=15 mm) into the skin, normally 4 mm, and measures the force required during a period of 20 seconds. Lindahl and Omata (1995) made a comparison between the impression method and a tactile sensor with regard to the ability of the two instruments to detect pitting oedema.

The tonometric methods are limited in that they cannot measure brawny oedema as they assume the fluid in the oedema is free flowing.

OBJECT OF THE INVENTION

The object of the present invention is to relieve or overcome the aforesaid problems and achieve a method and a device for measurement of oedema with regard to a combination of pitting oedema and brawny oedema.

BRIEF DESCRIPTION OF THE INVENTION

This objective is achieved using a method and a device to evaluate and/or distinguish pitting and/or non-pitting oedema.

According to one aspect of the present invention, a method for measurement of oedema comprises reading of a frequency of a freely oscillating resonance oscillating sensor, the resonance oscillating sensor being applied in use against an oedema to a certain depth of depression, the force of application and the resonance frequency of the resonance oscillating sensor being continuously read, whereby information concerning the degree of hardness is obtained as a measure of brawny oedema through read frequency shift and information concerning the degree of displaced fluid is obtained as a measure of pitting oedema through measurement of decay of force.

According to another aspect of the present invention, a device for measurement of oedema comprises a measuring head supported by a stand, wherein the measuring head includes a freely oscillating resonance oscillating sensor for making a resonance system together with the oedema when applied to the oedema, a reading unit to read current resonance frequency of the sensor, a force measurement device for measuring the force with which the sensor is applied to the oedema, whereby information concerning the degree of hardness is obtained as a measure of brawny oedema through read frequency shift and information concerning the degree of displaced fluid is obtained as a measure of pitting oedema through measurement of decay of force.

According to yet another aspect of the present invention, a device for measuring oedema comprises a measurement head including a first sensor to measure a first characteristic of the oedema and a second sensor, mounted adjacent to the first sensor, to measure a second characteristic of the oedema, so as to distinguish brawny oedema from pitting oedema.

These and other distinctive features and benefits will be obvious to a skilled person taking notice of the following detailed description of the embodiments of the invention that do not limit the scope of protection of the invention.

The embodiments are described with reference to the attached drawings, in which identical or similar parts have been given the same reference designations.

DETAILED DESCRIPTION OF EMBODIMENTS OF THE INVENTION

Generally, the arrangement for measurement of an oedema comprises a tactile sensor for measuring hardness/stiffness combined with the measurement of the reduction in the force required to depress tissue, e.g. skin or organ. This combination provides information partly relevant to the degree of hardness by measurement with the tactile sensor, and information partly related to the amount of displaced fluid in the tissue by measurement of the decay of force.

With this arrangement, the decay of force in relation to the change in hardness can be used as a measure of the size of the oedema, where the size of the oedema comprises an evaluation of both the fluid content and brawn.

Unlike known methods, such an arrangement can:

Evaluate and locate local occurrences of brawny oedema

Evaluate the results of treatment where brawny oedema are mobilised, e.g. through massage, and change to pitting oedema.

Evaluate the degree of pitting in relation to brawn

Figure 1:
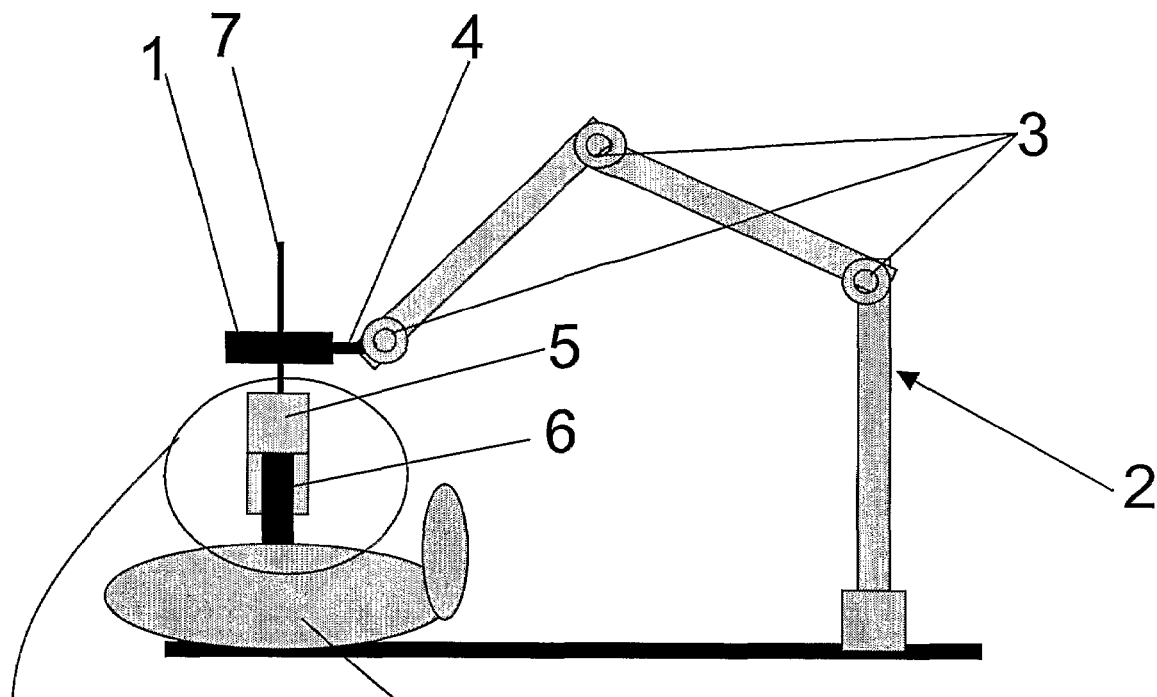
FIG. 1 shows a schematic view of an arrangement according to a first embodiment of the present invention.

The embodiment according to FIG. 1 illustrates a measuring setup with a stable stand 2 exhibiting securable flexible jointed arms for positioning of a measuring head. The arms are attached with lockable joints 3. A stepping motor 1 is arranged at one free end of the stand and can by means of computer control, not shown, be made to move the measuring head by means of a shaft 7 against the skin of a patient where oedema is located, e.g. a human leg 8. The measuring head comprises a resonance sensor 6, which can be of a piezoelectric material. The resonance sensor 6 is made to vibrate at a known resonance frequency using an electric feedback circuit, which feeds back the vibration via a relatively smaller piezoelectric element built into 6. The difference between the frequency of a freely oscillating sensor and the frequency when the sensor is pressed against tissue is called $\Delta f$ and is a measure of the acoustic impedance of the tissue, i.e. the hardness or stiffness of the tissue.

There is also a force sensor 5. The force sensor 5 is connected to the resonance sensor 6 so that the force that arises through the application of the resonance sensor 6 against the skin 13 can be registered without the force sensor 5 interfering with the vibration of the sensor 6. This can be achieved by casting the sensor 6 into an elastic sleeve 10 made, for example, of crude rubber, that allows the sensor to vibrate freely. The sleeve 10 can then be enclosed in a larger sleeve by means of spring washers 9, which allow the sleeve 10 to enable the force sensor 5 to measure the sensor's application force without affecting its vibration.

Figure 2:
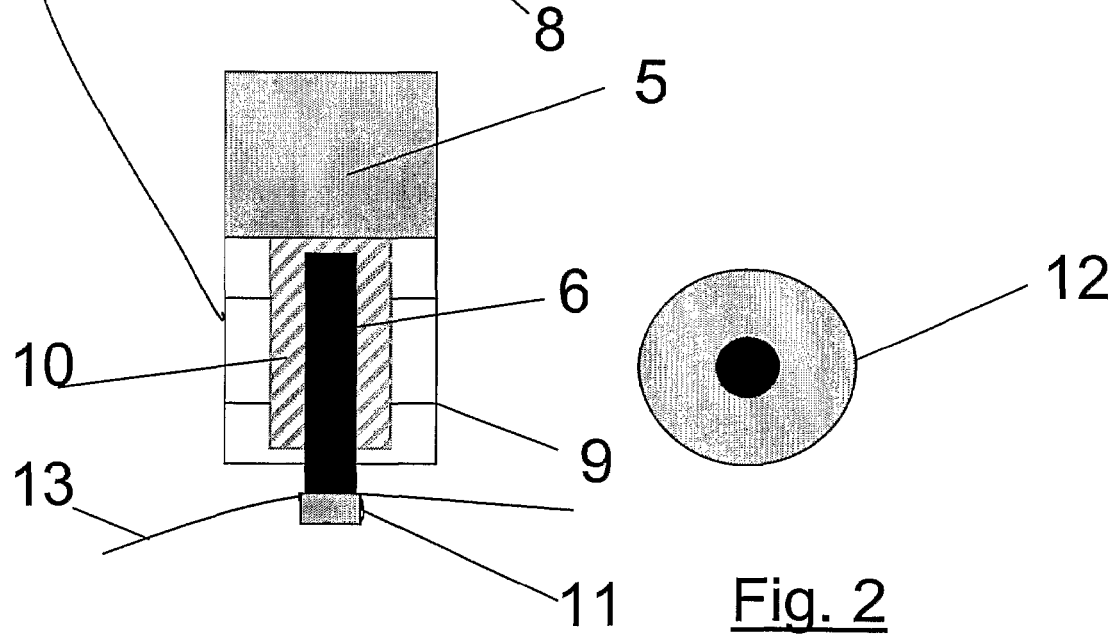
FIG. 2 shows the measuring head according to FIG. 1 in larger scale and partial cross-section.

The stepping motor 1, the force sensor 5 and the resonance sensor 6 are all connected via interface electronics to a personal computer, not shown, which controls and measures via software. When the sensor package 5, 6 in FIGS. 1 and 2 reaches the surface of the skin 13 on the leg 8, the force sensor 5 indicates that the surface has been reached through deflection of the force sensor, e.g. 50 mN. The motor 1 is then instructed by the computer to press in the measuring plate 11 to a certain depth in the skin, e.g. 4 mm. The measuring plate 11 has a known application surface, e.g. a circular cross section 12 of 15 mm. This leads to the measuring plate 11 achieving a depression in the skin corresponding to a cylinder of diameter 15 mm and height 4 mm. The volume of depressed skin can then be calculated according to $V=\pi h(D/2)^2=\pi 4(15/2)^2 0.707$ ml. By measuring the decay of the force over a period of time, e.g. 20 seconds, volume-related parameters can be calculated, e.g. as $V(t)=(1-Fn(t))\pi h(D/2)^2$ where Fn is normalised force, which provides information on the amount of free flowing fluid in the tissue that has been depressed.

To achieve a cylindrical depression, it is necessary for the measuring plate 11 to be parallel with the surface of the skin 13. This can be ensured with the stepping motor 1 and shaft 7 being fixably moveably arranged 4 on the stand, which allows the measuring plate to be adjusted so that it is parallel with the surface of the skin before application against it.

With this embodiment the hardness of the tissue can be measured with the resonance sensor at the same time as the volume of the free-flowing fluid can be estimated. Thus, a combined pitting and brawny oedema can be measured.

In an alternative embodiment, measuring can be done with the motor driven sensor package 1, 5, 6, 7 in a hand-held version without the fixed stand in FIG. 1. In this embodiment, the stand can be a counter hold arrangement, e.g. a rim arranged on the motor sensor package and furnished with one or more supporting points arranged to support on the skin/tissue around, but at a distance from, the tip of the sensor so that a sustained depression safely can be achieved for at least 20 seconds without dislodging the sensor package. The distance from the tip of the sensor is adjusted so that the supporting points do not affect the tissue in which measurements are being done.

In a further embodiment, the measuring head 5, 6 can be arranged manually displaceable to the stand, so that it exhibits two mechanically limited positions: one starting position and one measuring position. When a measurement is to be taken, the measuring head is in its starting position and the stand is adjusted so that the application surface of the resonance sensor 6 is parallel to, and flushes with, the tissue to be measured. After that the measuring head is displaced manually to its active measuring position and measurement can start. Hereby a certain depth of depression is obtained without adjustable electric stepping motors. Mechanical application, however, does not offer the flexibility concerning the desired depth of depression that the adjustable stepping motor does.

When using the method according to the present invention simultaneous reading of frequency shift $\Delta f$ and force F can be done, whereby a parameter $\Delta f/F$ can be calculated that describes the consistency of the oedema or the relative relationship between pitting and brawn. This simultaneous reading can be done continuously and e.g. be plotted as $\Delta f$ vs. F, whereby the incline can constitute a measure of the consistence of the oedema.

The invention claimed is:

1. A method of measuring oedema in a patient, the method comprising:

pressing a surface of an oscillating resonance sensor against the skin surface of the patient to a certain depth;

simultaneously reading with a force sensor a force required to depress the skin surface to the certain depth and a frequency of the oscillating resonance sensor over a period of time;

determining a difference $\Delta f$ between the oscillating resonance sensor frequency reading and a known resonance frequency of the oscillating resonance sensor that occurs when the oscillating resonance sensor freely oscillates as a measure of brawny oedema; and determining a decay in the force F required to depress the skin surface to the certain depth as a measure of pitting oedema.

2. A method according to claim 1, further comprising:
presenting the frequency readings and the force readings.

3. A method according to claim 1, further comprising:
calculating a parameter $\Delta f/F$ that describes a relative relationship between pitting oedema and brawny oedema.

4. A method according to claim 3, wherein simultaneously reading the force and the frequency comprises continuously reading the force and the frequency, and the method further comprises:

plotting a curve corresponding to the parameter Δf/F, wherein an inclination of the curve corresponds to a measure of the relative relationship between pitting oedema and brawny oedema.

5. A method according to claim 1, wherein the oscillating resonance sensor surface has a circular cross section.

6. A method according to claim 5, wherein the oscillating resonance sensor surface has a diameter of 15 mm.

7. A method according to claim 1, wherein the period of time comprises 20 seconds.

8. A method according to claim 1, wherein the certain depth comprises 4 mm.

9. A method according to claim 1, wherein the surface of the oscillating resonance sensor is parallel to the skin surface when pressed.

10. A device for measuring oedema in a patient, comprising:

a measuring head, the measuring head comprising
an oscillating resonance sensor, the oscillating resonance sensor comprising a surface configured to be pressed against a skin surface of the patient, and
a force sensor, wherein the oscillating resonance sensor is connected to the force sensor so that the oscillating resonance sensor is operable to oscillate without interference from the force sensor; and
an adjustable stand that adjustably supports the measuring head.

11. A device according to claim 10, wherein the control is further configured to calculate a parameter Δf/F that describes a relative relationship between pitting oedema and brawny oedema.

12. A device according to claim 11, wherein control is configured to continuously simultaneously read the force and the frequency, and plot a curve corresponding to the parameter Δf/F, and an inclination of the curve corresponds to a measure of the relative relationship between pitting oedema and brawny oedema.

13. A device according to claim 10, further comprising means for adjusting the measuring head.

14. A device according to claim 13, wherein the adjusting means comprises a stepping motor.

15. A device according to claim 10, further comprising means for presenting the oscillating resonance sensor readings and the force sensor readings.

16. A device according to claim 15, wherein the presenting means comprises a computer.

* * * * *